(12) United States Patent
DiMino et al.

(10) Patent No.: US 11,419,785 B2
(45) Date of Patent: Aug. 23, 2022

(54) DIGITAL TINNITUS TREATMENT ELECTRONIC HEADSET SYSTEM AND METHOD FOR OPERATION OF SAME

(71) Applicant: ADM Tronics Unlimited Inc, Northvale, NJ (US)

(72) Inventors: Andre' A. DiMino, Northvale, NJ (US); Matthew E. Drummer, Fort Lee, NJ (US)

(*) Notice: Subject to any disclaimer, the term of this patent is extended or adjusted under 35 U.S.C. 154(b) by 596 days.

(21) Appl. No.: 16/439,678

(22) Filed: Jun. 12, 2019

(65) Prior Publication Data
US 2019/0374427 A1    Dec. 12, 2019

Related U.S. Application Data

(60) Provisional application No. 62/683,701, filed on Jun. 12, 2018.

(51) Int. Cl.
*A61H 23/02*     (2006.01)
*A61F 11/00*     (2022.01)
*A61B 5/12*      (2006.01)

(52) U.S. Cl.
CPC .......... *A61H 23/0245* (2013.01); *A61F 11/00* (2013.01); *A61B 5/128* (2013.01); *A61H 2201/5005* (2013.01); *A61H 2205/027* (2013.01)

(58) Field of Classification Search
CPC ...... H04R 1/1066; H04R 5/033; H04R 25/75; H04R 25/00; A61H 23/0245; A61H 23/00; A61H 23/004; A61H 23/006; A61H 23/02; A61F 11/00; A61B 5/12; A61B 5/128
See application file for complete search history.

(56) References Cited

U.S. PATENT DOCUMENTS

| 5,788,656 A | 8/1998 | DiMino | |
| 6,210,321 B1 * | 4/2001 | Di Mino | A61F 11/00 600/28 |
| 7,347,827 B2 * | 3/2008 | Choy | A61M 21/00 600/559 |
| 2008/0112581 A1 * | 5/2008 | Kim | H04R 1/1075 381/151 |
| 2008/0132752 A1 | 6/2008 | Choy | |
| 2011/0058696 A1 * | 3/2011 | Armstrong | H04R 5/033 381/309 |
| 2014/0126752 A1 * | 5/2014 | Beck | A61N 1/3603 381/151 |

(Continued)

FOREIGN PATENT DOCUMENTS

| EP | 0537385 A1 * | 4/1993 | A61B 5/12 |
| WO | 2017040747 A1 | 3/2017 | |

*Primary Examiner* — Joseph D. Boecker
*Assistant Examiner* — Thomas W Greig

(57) ABSTRACT

The present invention relates to an electronic headset system which is preferably wirelessly controlled, and is used to treat a tinnitus disorder. The system in an electronic headset and preferably an electronic communication device, such as a smartphone, laptop, tablet, desk top computer, server, and the like or any combination thereof. The electronic headset includes a treatment probe and emits complex signals which are converted into vibrations by the treatment probe and are transmitted to a users cochlea via the treatment probe communicating with the user's mastoid bone when the electronic headset is worn, thereby alleviating the symptoms of the user's tinnitus disorder.

22 Claims, 5 Drawing Sheets

(56) References Cited

U.S. PATENT DOCUMENTS

| | | |
|---|---|---|
| 2016/0021471 A1 | 1/2016 | Davis et al. |
| 2017/0171677 A1 | 6/2017 | Norris et al. |
| 2017/0353807 A1* | 12/2017 | Lim ................. A61B 5/128 |
| 2017/0368329 A1* | 12/2017 | Tyler ................. A61M 21/00 |
| 2018/0271710 A1* | 9/2018 | Boesen ............. A61B 5/128 |

* cited by examiner

DIGITAL TINNITUS TREATMENT ELECTRONIC HEADSET SYSTEM AND METHOD FOR OPERATION OF SAME

The present application claims the benefit of U.S. Provisional application No. 62/683,701, entitled "TINNITUS TREATMENT ELECTRONIC HEADSET, AND METHOD FOR OPERATION OF SAME", filed on Jun. 12, 2018, which is incorporated herein by reference in its entirety.

BACKGROUND OF THE INVENTION

1. Field of the Invention

The present invention relates to a digital electronic headset system which is preferably wirelessly controlled, and is used to treat a tinnitus disorder. The system includes an electronic headset and preferably an electronic communication device, such as a smartphone, laptop, tablet, desk top computer, server, and the like or any combination thereof. Although the electronic communication device is preferably wireless, the electronic communication device can also be embedded in or directly connected to the electronic headset via a wire or some other direct connection such as an electronic coupling. The electronic headset includes a treatment probe, and emits complex signals which are converted into vibrations by the treatment probe and are non-invasively transmitted to a user's cochlea when the electronic headset is worn, thereby alleviating the symptoms of the user's tinnitus disorder.

2. Description of the Related Arts

Tinnitus is a disorder more commonly known as ringing of the ears. Though the term refers to sounds originating in the ear, the sounds may not be ringing in nature, for buzzing, humming, whistling and roaring sounds are also indicative of a tinnitus disorder. A more precise definition of tinnitus is any sound sensation for which there is no source outside of the individual.

Conventional tinnitus treatment devices on the market have many shortcomings as the conventional devices are bulky, cumbersome for a user to use, and provide little or no medical feedback information to a user and the user's medical provider. What conventional tinnitus treatment technology is lacking is an easy to use, statistical gathering device that can be controlled and monitored by the user and the user's medical provider.

SUMMARY OF THE INVENTION

The present invention addresses the above shortcomings of conventional tinnitus treatment technology and relates to an electronic headset system which is both effective for the treatment of tinnitus disorders, and able to gather information and statistics pertaining to a users treatment The electronic headset system of the present invention includes a headset having a first section, a second section and a third section which are adjustably connected to each other. However the first section, second section, and third section can also be fixed to each other or designed as and incorporated into a single unit. The first section includes a first lateral support which is positioned laterally against a person's head. The second section includes a head cap which fits over the crown of a person's head. The third section includes a second lateral support which is positioned laterally against a person's head diametrically opposite to the first lateral support, an electronics section is connected to the second lateral support at an angle but other connection configurations may be used, including the electronics section functioning as the second lateral support by being incorporated into the second lateral support. The electronics section has at least one of an electronic communication circuit and an electronic treatment signal circuit which emits complex signals. Although the third section includes the electronics section, this is for convenience of illustration only and the electronics section can be included partially or wholly in the first section, second section, third section, separately, or in any combination thereof. The third section further includes a treatment probe section that includes a transducer and a treatment probe. The treatment probe section is connected to the electronics section at preferably 135 degree angle but other connection angles can be used. The treatment probe section includes the treatment probe connected to a base of the treatment probe section at preferably a 90 degree angle to the treatment probe section but other angles may used.

The treatment probe receives the complex signals from the electronic treatment signal circuit and converts the signals into vibrations which are communicated to a user's cochlea via the mastoid part of a user's temporal bone, herein referred to as "mastoid bone", by contacting or being positioned near the mastoid bone when the electronic headset is worn, thereby alleviating the symptoms of the user's tinnitus disorder. The treatment probe is preferably positioned by the user to communicate with the mastoid bone by contacting or being positioned near the mastoid bone. The combination of connection angles of the treatment probe section and the treatment probe ensures accurate and easy positioning of the probe in proximity to a user's mastoid bone by a user. Although the headset is illustrated as having three sections, the headset may be constructed as having a single section, two sections, or more than three sections, The electronic headset system further includes an electronic communication device, such as a smartphone, laptop, tablet, desk top computer, server, and the like or any combination thereof. The electronic communication device is used to control settings of the headset such as frequency, amplitude and output strength of the vibration of the treatment probe. The electronic communications device can collect data and transmit/receive the data to the headset. Although the headset system includes an electronics communication device, this is for convenience of illustration only. In another embodiment the headset can be made with a display screen such as a LED screen, a LCD screen or the like and can include electronic circuits which can be used to control settings, collect data and transmit/receive data to other electronic devices.

Another embodiment of the present invention includes the third section being configured to position the treatment probe in proximity to a user's mastoid bone so that when the treatment probe is activated by the treatment signal circuit, vibrations are produced which are transmitted by bone conduction to a user's inner ear.

Another embodiment of the present invention includes an electronic communications device connected to the electronic communications circuit of the third section so that signals generated from the electronic communications device are received by the electronic communications circuit and are used to adjust the frequency, amplitude, and output strength of the signals which are generated by the treatment signal circuit to control vibration of the treatment probe.

Another embodiment includes a method for operating the headset. A user puts the headset on their head, and adjusts the position of the treatment probe to be in communication with their mastoid bone The user uses an app on an electronic communications device such as a smartphone to adjust the frequency, amplitude, and output strength of the signals emitted by the treatment signal circuit which controls vibration until the user feels relief from the ringing in their ears. The settings are saved in a user history file either in the headset, the app, the cloud, or any combination thereof. A medical provider can access the settings of the headset to configure the headset settings, and can access the user history of a user to monitor the user's progress.

The above and yet other objects and advantages of the present invention will become apparent from the hereinafter set forth Brief Description of the Drawings and Detailed Description of the Invention.

It is intended that any other advantages and objects of the present invention that become apparent or obvious from the detailed description, drawings or illustrations contained herein are within the scope of the present invention. It is also intended that any feature and limitation listed in an embodiment of the present invention can be used in any other embodiment of the present invention unless specifically stated otherwise.

BRIEF DESCRIPTION OF THE DRAWINGS

The above and other object and features of the present invention will become better understood with regard to the following description of the embodiments given in conjunction with the accompanying drawings, in which.

It is intended that any feature of any embodiment of the present invention can be included as a feature in another embodiment of the present invention unless stated otherwise.

It is further intended that any other embodiments of the present invention that result from any changes in application or method of use or operation, method of manufacture, shape, size or material which are not specified within the detailed written description or illustrations and drawings contained herein, yet are considered apparent or obvious to one skilled in the art, are within the scope of the present invention.

DETAILED DESCRIPTION OF THE INVENTION

Figure 1:
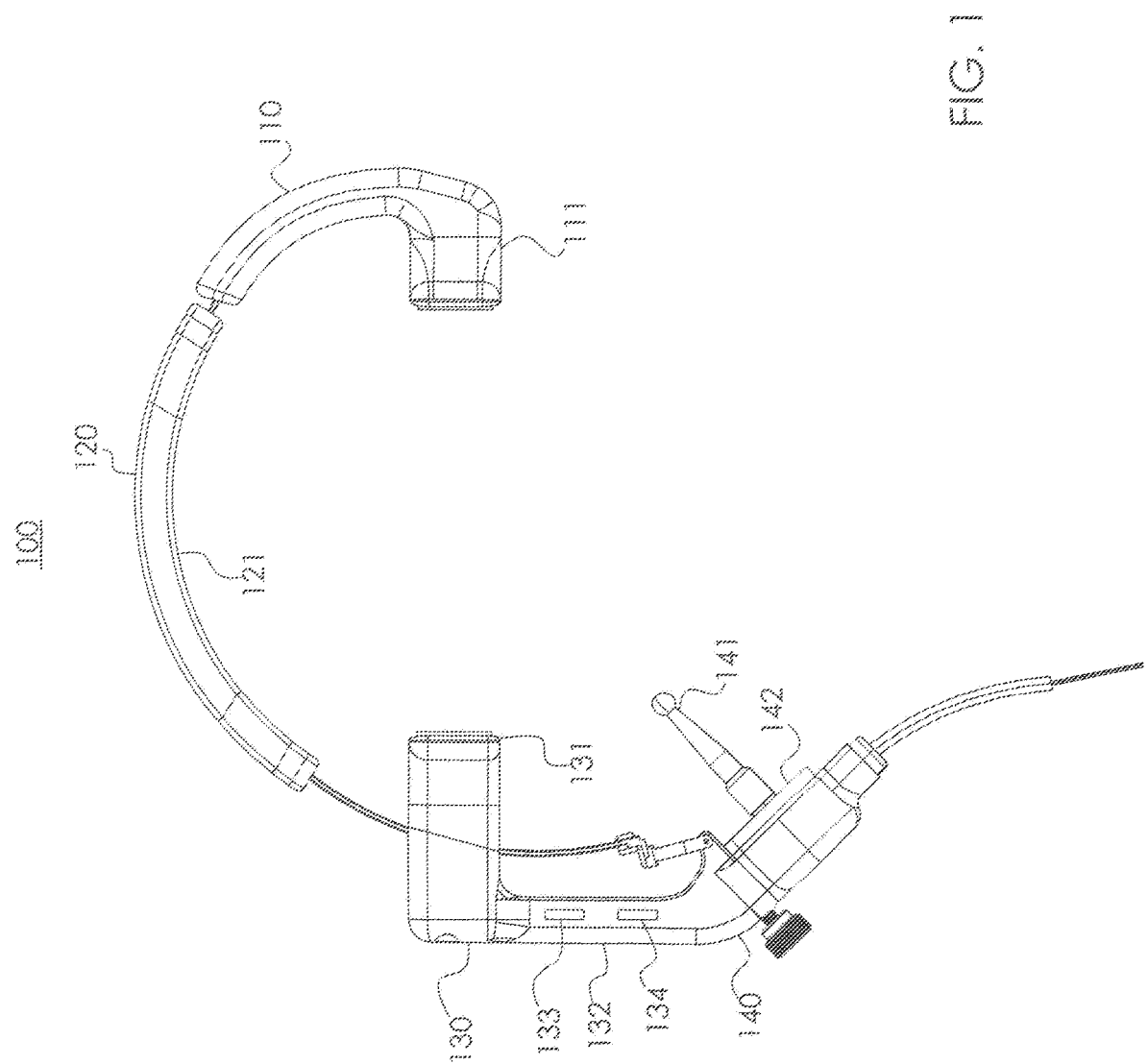
FIG. 1 is a front view illustrating a headset according to an embodiment of the present invention.
Figure 2:
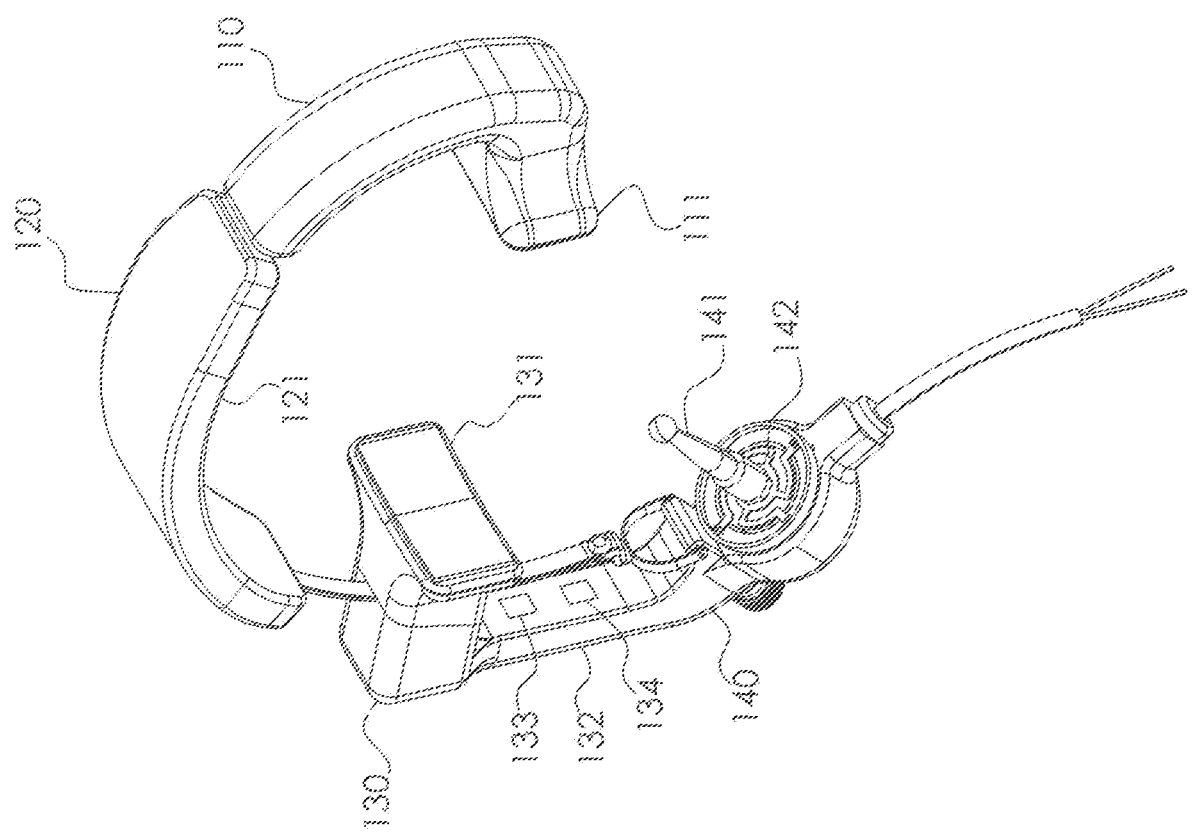
FIG. 2 is an isometric view of the headset in figure FIG. 1.

Hereinafter, a preferred embodiment of the invention will be described in detail along with the accompanying drawings, The electronic headset includes a treatment probe and emits complex signals which are converted into vibrations by the treatment probe and are transmitted to a user's cochlea via the treatment probe being in communication with the mastoid bone when the electronic headset is worn, thereby alleviating the symptoms of the user's tinnitus disorder. The electronic headset system allows a user and a user's medical provider to adjust the settings of the electronic headset and capture user treatment information such as the electronic headset's treatment settings, the effectiveness of particular treatment settings, and historical data related to the use of the electronic headset by a user, FIG. 1 is a front view illustrating a headset according to an embodiment of the present invention. FIG. 2 is an isometric view of the headset in figure FIG. 1.

As shown in figures FIG. 1 and FIG. 2, the headset 100 includes a first section 110, a second section 120, and a third section 130 which are adjustably connected to each other however the sections can also be fixed in relation to each other or any combination of adjustable and fixed positioning thereof can be used.

The first section includes a first lateral support 111 which is positioned laterally against a person's head. The second section includes a head cap support 121 which fits over the crown of a person's head. The third section 130 includes a second lateral support 131 which is positioned laterally against a person's head diametrically opposite to the first lateral support 111, an electronics section 132 connected to the second lateral support 131 at a right angle but other connection angles may be used, including the electronics section 132 functioning as the second lateral support 131. The electronics section 132 includes an electronic communication unit 133 and an electronic treatment signal unit 134 which emits signals. The electronic communication unit 133 and the treatment signal unit 134 may include all circuits, systems, firmware and devices necessary for their respective operations and functions.

The treatment signal unit 134 produces a combination of complex signals to vibrate the treatment probe which when the headset is worn by a user is in communication with the user's mastoid bone, at a frequency combination that surrounds the perceived frequency of the user's tinnitus. The applied combination of vibratory frequency applies the mechanism of noise cancellation to reduce or silence the user's perception of the user's perceived tinnitus sound. The electronic treatment signal unit 134 allows the user to tune the parameters of the frequency and a beat frequency that occur when the combination of signals intersect. The complex signals generated by the electronic treatment signal unit 134 may be configured in accordance with the disclosures made in U.S. Pat. Nos. 6,210,321 and 5,788,656 issued to DiMino et. al. which are herein incorporated by reference in their entirety. However, other methods of configuring the complex signals may be used. Although the third section 130 includes the electronics section 132, this is for convenience of illustration only and the electronics section 132 can be included partially or wholly in the first section, second section, third section, separately, or any combination thereof.

The treatment signal unit 134 further includes microprocessor (not shown) that controls the creation of a set of signals and allows for the control of parameters such as frequency, amplitude, output strength, beat frequency which will be tuned by the user or a medical provider. Additionally, the treatment signal unit may include power circuits (not shown), recharging circuits (not shown), a power supply 143, and electronic connections to a transducer 142 which vibrates the treatment probe. The power supply 143 can be, but is not limited to, alternating current (A/C), any type of battery power, or any combination thereof.

The third section 130 further includes a treatment probe section 140 which is connected to the electronics section 132 at preferably 135 degree angle but other connection angles can be used. The treatment probe section 140 includes a treatment probe 141 connected to the transducer 142 at preferably a 90 degree angle to the treatment probe section 140 but other angles may used. Preferably the treatment probe 141 can be female threaded and screwed onto a male threaded portion of the transducer 142 but other connections to the transducer 142 can be used. The treatment probe 141 receives the complex signals from the treatment signal unit 134 and converts the signals into vibrations which are communicated to a user's cochlea via the user's mastoid bone when the electronic headset is worn, thereby alleviating the symptoms of the user's tinnitus disorder. The combination of connection angles of the treatment probe section 140, the treatment probe 141 and the transducer 142 ensures accurate and easy positioning of the treatment probe 141 to a user's mastoid bone. Once a user feels relief from their tinnitus symptoms, then for future use, the user can choose to save the headset settings in the headset, in the electronic communications device, in the cloud, or in any combination thereof.

Figure 3:
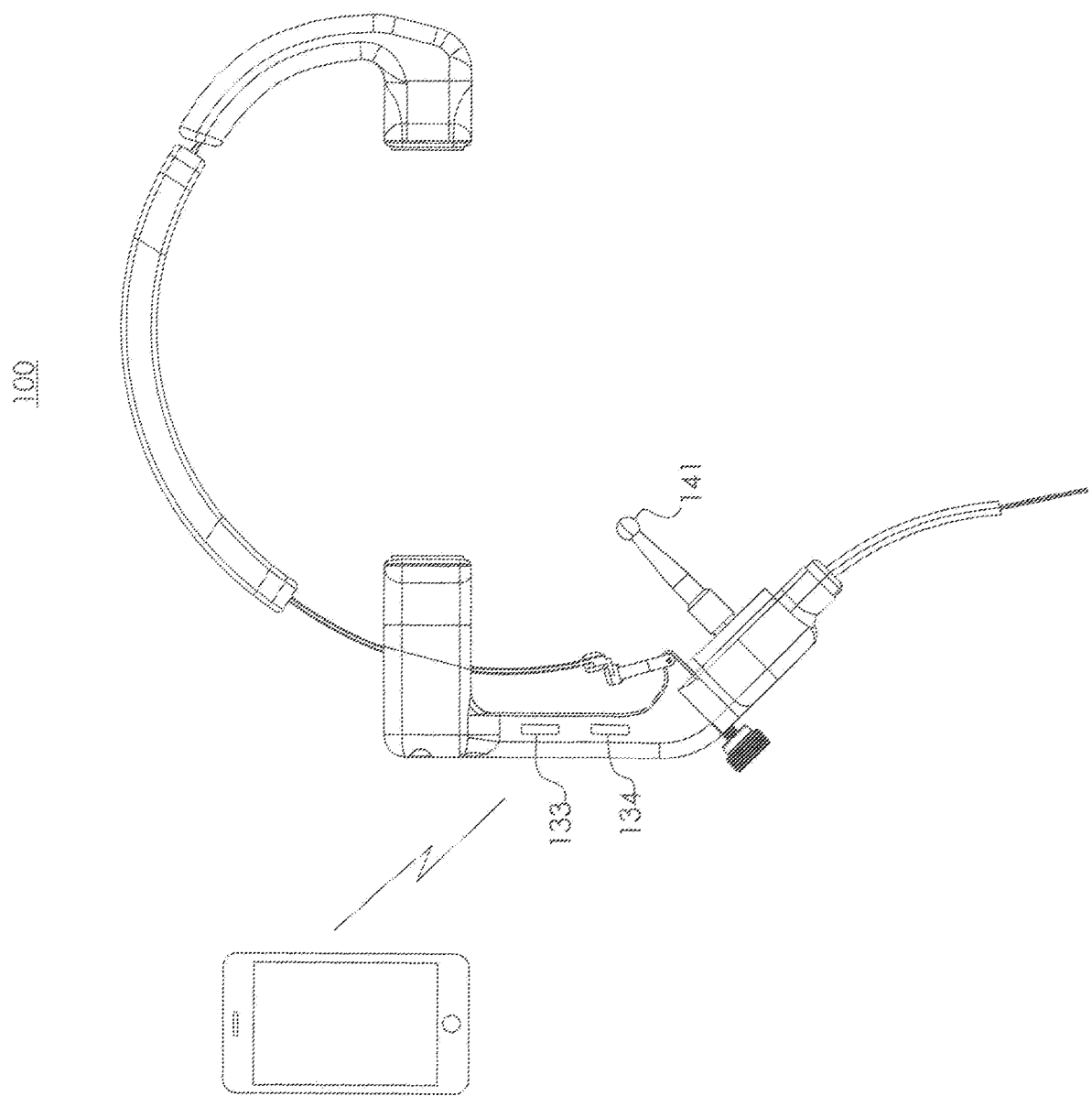
FIG. 3 is an illustration of the headset system according to an embodiment of the present invention.

FIG. 3 is an illustration of the headset system according to an embodiment of the present invention.

The headset 100 includes an electronic communication unit 133 and a treatment signal unit 134 which emits complex signals. A user executes an app (not shown) on an electronic communication device 301 such as a smartphone, a laptop, a tablet, or similar device in order to gain access to the configuration settings for the headset 100. The app interfaces, preferably wirelessly, with the headset 100 to adjust the settings for emitting the complex signals. However, in another embodiment, the app can be stored in the headset, and can be accessed and adjusted directly from the headset. The app will record the date and time of the treatment. The app has controls to adjust the combination of frequencies and has an amplitude control to control the strength or volume of the vibration. The app will have communication section to allow the data to be saved, to allow the data to be sent to a medical provider as well as to allow the medical provider to adjust the headset settings remotely. The app will also have sections which allow for searching for tinnitus related information, creation of a community on the app for tinnitus sufferers, and allow users to communicate their progress and suggestions about the use of the tinnitus treatment headset system, The user puts on the headset so that the treatment probe 141 is in proximity to or rests on the user's mastoid bone. The user adjusts the settings in the app until the treatment probe 141 receives the signals emitted by the treatment signal unit 134 and converts the signals into vibrations which are applied to and picked up by the user's mastoid bone to alleviate the user's tinnitus symptoms. Since not all users are the is same, the settings established for one user may be entirely different from the settings established for another user. In an embodiment, the app will capture user data such as signal frequency settings, usage duration, and effectiveness of the treatment in relieving the symptoms of tinnitus. In another embodiment, a medical provider will be able to access the user's data and make modifications to the settings in order to evaluate the effectiveness of the headset 100 in alleviating the user's symptoms of tinnitus.

Figure 4:
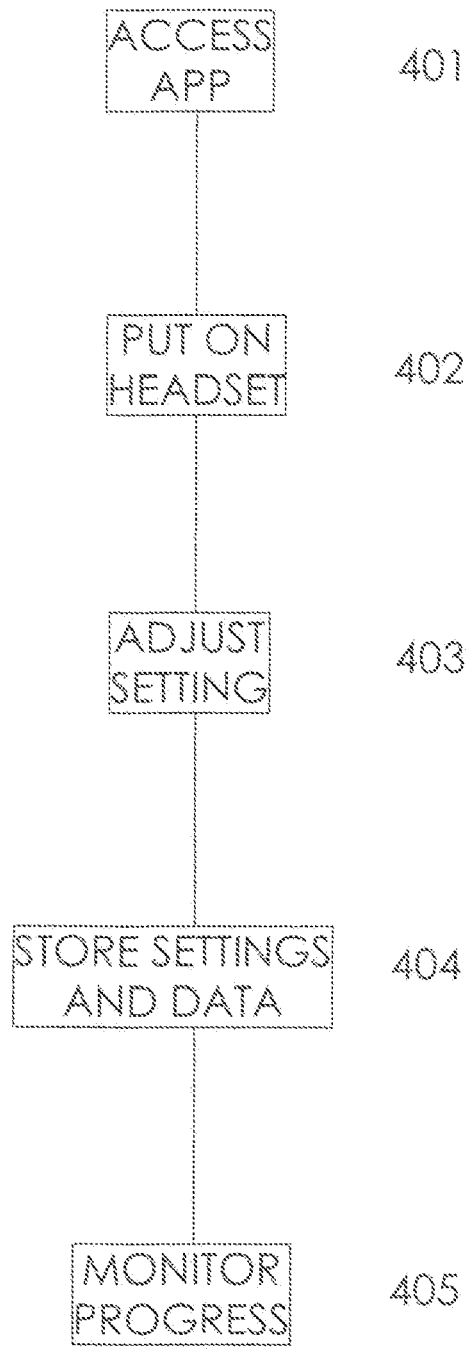
FIG. 4 is an illustration of a method for operating the headset system.

FIG. 4 is an illustration of a method for operating the headset system.

Referring to figure FIG. 4, in step 401 a user accesses an app on an electronic communications device such as a smartphone. Initially, the user uses the app to "hear" their own tinnitus noise. This is accomplished by the app having a tinnitus sound simulator that can let the user listen to the app and approximate the frequency of the user's own tinnitus noise. Through this, the user can then try to match their tinnitus noise by applying a similar frequency to the vibratory treatment probe. By applying a matched frequency of the vibration, the treatment probe of the headset will cause noise cancellation to reduce or eliminate the user's perception of their tinnitus. As is known in acoustics, by applying an opposite sine wave the original sound is cancelled.

Due to the complex nature of the signal, the app will produce a beat-frequency heard by the user when the signals intersect. This beat frequency assists in treating the tinnitus. After the user finds the appropriate matching cancellation signal, the user then sets the amplitude or power of the vibration to achieve the highest comfortable level of vibration that the user can endure without pain. The user will then treat their tinnitus, preferably 3 to 5 minutes for each treatment session, preferably 2 to 3 times per day. Over time, based on the residual inhibition the user achieves, the user can reduce the number of treatments to one a day, once every few days and in some cases once every few weeks or longer. The data for each treatment session such as date, time, duration, settings, etc., are stored in the app but can also be stored in the headset, in the electronic communications device, in the cloud, or in any combination thereof. The medical provider can use the app to read the data remotely and if desired, can also set the parameters of the headset for the user's treatment.

In step 402 the user puts the headset on their head. In step 403 the user changes the settings for the headset using the app on the smartphone or within the headset to control the settings of the treatment signal unit of the headset. In another embodiment, headset can include controls for adjusting the settings of the headset independently of using an app. In yet another embodiment, the headset can be configured with a LED, a LCD screen or the like in order for the user to interface with headset and configure the headset's settings. In step 404 once the user has found settings that provide relief to the user's tinnitus symptoms, the settings data and the user's usage data are stored by the app. The data can be stored in the cloud, in the smartphone, in the headset or in any combination thereof. Furthermore, in step 405 a medical provider can then access the user's stored data via the smartphone app in order to monitor the user's treatment progress.

Figure 5:
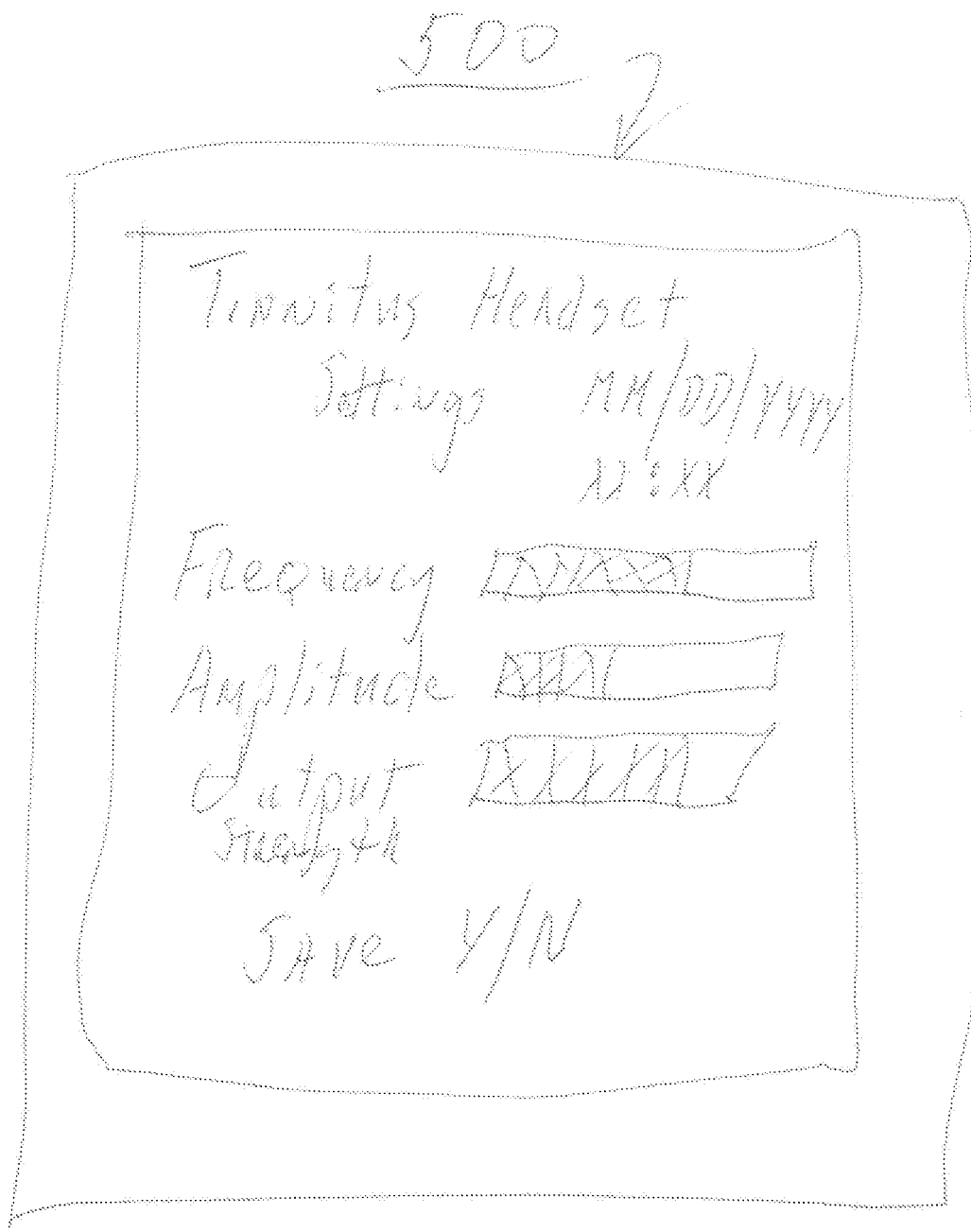
FIG. 5 is an illustration of an example of a display screen displayed to a user for adjusting the settings of the headset according to an embodiment of the present invention.

FIG. 5 is an illustration of an example of a display screen displayed to a user for adjusting the settings of the headset according to an embodiment of the present invention.

Referring to FIGS. 3, 4 and 5, to adjust the headset settings 403, a user can visually view on a display screen 500 their current headset setting configuration as shown in FIG. 5. The display screen 500 can be in the electronic device 301 which is used to access the headset, can be in tie headset 100, or can be in any combination thereof. Furthermore, once a user feels relief from their tinnitus symptoms, the user is given an opportunity to save the current headset settings 404. Additionally, saying the settings allows a medical professional to evaluate the treatment progress made by a particular user.

While the present invention has been described with respect to certain preferred embodiments, it will be apparent to those skilled in the art that various changes and modifications may be made without departing from the scope and spirit of the invention.

Embodiments of the present invention hake been described with reference to the accompanying drawings, and specific terms or words used in the description should be construed in accordance with the spirit of the present invention without limiting the subject matter thereof. It should be understood that many variations and modifications of the basic inventive concept described herein will still fall within the spirit and scope of the present invention as defined in the appended claims and their equivalents.

What is claimed is:

1. A headset system for canceling tinnitus noise comprising:
   an electronic circuit configured to generate control signals according to parameters set by a user;
   a transducer configured to receive the control signals generated by the electronic circuit and to vibrate in accordance with the received control signals; and
   a treatment probe connected to the transducer and which vibrates in conjunction with the transducer,
   wherein the electronic circuit, the transducer, and the treatment probe are integrated into a headset,
   wherein a position of the treatment probe is adjusted by a user when setting the parameters for the electronic circuit so that the user optimizes noise cancellation of the tinnitus noise,
   wherein the headset includes a first section configured to be worn on a head of the user, and a second section which includes the treatment probe,
   wherein the first section and the second section are a single headset unit, and
   wherein the second section is connected to the first section at a fixed angle of 135 degrees relative to the first section.

2. The headset system according to claim 1, wherein optimization of the noise cancellation of the tinnitus noise includes matching a frequency of the vibration generated by the treatment probe with a frequency of the tinnitus noise.

3. The headset system according to claim 1, wherein optimization of the noise cancellation of the tinnitus noise includes applying an opposite sine wave which is generated by the vibrations of the treatment probe to the tinnitus noise so that the tinnitus noise is cancelled.

4. The headset system according to claim 1, wherein a user adjusting a position of the treatment probe when setting the parameters for the electronic circuit includes the user adjusting a position of the treatment probe so that the treatment probe is in communication with the user's mastoid bone.

5. The headset system according to claim 1, further comprising an electronic device configured to set the parameters which generate the control signals from the electronic circuit.

6. The headset system according to claim 5, wherein the electronic device is at least one of integrated into the headset and separate from the headset.

7. The headset system according to claim 1, wherein the first section includes the electronic circuit.

8. The headset system according to claim 1, wherein the treatment probe is connected to the second section at a fixed angle.

9. The headset system according to claim 1, wherein the treatment probe is connected to the second section at an adjustable angle.

10. The headset system according to claim 1, wherein power is supplied to the headset via at least one of a battery and A/C current.

11. The headset system of claim 1, wherein the second section further includes the electronic circuit and the transducer.

12. A method of canceling tinnitus noise using a headset which includes an electronic circuit, a transducer, and a treatment proble, the method comprising;
   generating control signals by the electric circuit according to parameters set by a user;
   receiving the control signals by the transducer so that the transducer vibrates a treatment probe in accordance with the received control signals; and
   adjusting a position of the treatment probe by the user so that noise cancellation of the tinnitus noise is optimized,
   wherein the headset includes a first section configured to be worn on a head of the user, and a second section which includes the treatment probe,
   wherein the first section and the second section are a single headset unit, and
   wherein the second section is connected to the first section at a fixed angle of 135 degrees relative to the first section.

13. The method of claim 12, wherein optimization of the noise cancellation of the tinnitus noise includes matching a frequency of the vibration generated by the treatment probe with a frequency of the tinnitus noise.

14. The method of claim 12, wherein optimization of the noise cancellation of the tinnitus noise includes applying an opposite sine wave which is generated by the vibrations of the treatment probe to the tinnitus noise so that the tinnitus noise is cancelled.

15. The method of claim 12, wherein adjusting a position of the treatment probe by the user includes the user adjusting the treatment probe so that the treatment probe communicates with the user's mastoid bone.

16. The method of claim 12, wherein generating control signals by the electronic circuit according to parameters set by a user includes the user using an electronic device to set the parameters.

17. The method of claim 16, wherein the electronic device is at least one of the integrated into the headset and separate from the headset.

18. The method of claim 12, wherein the first section includes the electronic circuit.

19. The method of claim 12, wherein the treatment probe is connected to the second section at a fixed angle.

20. The method of claim 12, wherein the treatment probe is connected to the second section at an adjustable angle.

21. The method according to claim 12, wherein power is supplied to the headset via at least one of a battery and A/C current.

22. The method of claim 12, wherein the second section further includes the electronic circuit and the transducer.

* * * * *